United States Patent [19]

Asano et al.

[11] Patent Number: 4,483,807
[45] Date of Patent: Nov. 20, 1984

[54] PROCESS FOR PRODUCING A SLOW RELEASE COMPOSITE

[75] Inventors: Masaharu Asano; Masaru Yoshida; Isao Kaetsu, all of Gunma, Japan

[73] Assignee: Japan Atomic Energy Research Institute, Tokyo, Japan

[21] Appl. No.: 340,989

[22] Filed: Jan. 20, 1982

[30] Foreign Application Priority Data

Jan. 27, 1981 [JP] Japan ................................ 56-10674
Jan. 30, 1981 [JP] Japan ................................ 56-12606
May 26, 1981 [JP] Japan ................................ 56-79567

[51] Int. Cl.$^3$ ............................................. H05B 6/64
[52] U.S. Cl. ....................................... 264/22; 264/28; 428/36; 428/177
[58] Field of Search ............... 264/4, 22, 28; 424/36, 424/177

[56] References Cited

U.S. PATENT DOCUMENTS

| | | | |
|---|---|---|---|
| 3,576,758 | 4/1971 | Emrick | 424/36 |
| 3,614,851 | 10/1971 | Green | 264/28 |
| 3,780,195 | 12/1973 | Balassa | 424/36 |
| 4,073,835 | 2/1978 | Otsuki et al. | 264/22 |
| 4,230,687 | 10/1980 | Sair et al. | 424/36 |
| 4,369,784 | 1/1983 | de Buman et al. | 264/28 |

FOREIGN PATENT DOCUMENTS 102827 of 1974 Japan.
42025 of 1975 Japan.

OTHER PUBLICATIONS

Mark, H., Journal of Applied Physics, vol. 20, p. 531 (1949).
Grant, N. H., Journal of American Chemical Society, vol. 85, p. 4071 (1966).

Primary Examiner—Paul Lieberman
Assistant Examiner—W. Thompson
Attorney, Agent, or Firm—Browdy and Neimark

[57] ABSTRACT

A process is herein disclosed for producing a slow release composite comprising grinding and mixing mechanically in a frozen state one or more polypeptides, one or more proteins and one or more physiologically active substances shaping the blend into a desired form and compressing at a pressure of from 100 to 20,000 kg/cm$^2$ to thereby produce a slow release composite having the physiologically active substances encapsulated therein.

4 Claims, 8 Drawing Figures

PROCESS FOR PRODUCING A SLOW RELEASE COMPOSITE

BACKGROUND OF THE INVENTION

Japanese published Patent Application (OPI) Nos. 102827/74 and 42025/75 (the symbol OPI as used herein means an unexamined published Japanese patent application) disclose processes for producing a slow release agent wherein a physiologically active substance is supported on protein from various protein sources such as collagen and gelatin. But the efficacy of the slow release agents prepared by such conventional methods lasts for only several hours to ten-odd days. In this respect, none of the slow release agents developed so far make the most of protein as a substance compatible with the living tissue.

SUMMARY OF INVENTION

The present inventors have made studies on a slow release agent that has a physiologically active substance supported on protein and which allows the physiologically active substance to exhibit its activity slowly over an extended period. One result of these studies is an invention of a process for producing a slow release composite having a physiologically active substance encapsulated in thermally denatured protein, and this invention has already been reported in an unpublished document. But this earlier process has a defect: the presence of water is generally necessary for thermally denaturing protein, and in the presence of water, the greater part of the resulting protein matrix is porous and the encapsulated physiologically active substance soon dissolves out of the matrix. In search for means to solve this problem, the present inventors have found that the slow releasability of the conventional product can be improved by encapsulating the physiologically active substance in polypeptide and filed a patent application for such idea.

The present invention should be understood as a further improvement of this idea. A film prepared by compressing fine particles of polypeptide under low temperatures is fairly viscous and has good film properties. But proteins such as milk casein and gelatin are more viscous than polypeptides, and the present inventors have found that a slow release composite having slower releasability of physiologically active substances can be produced by using both polypeptide and protein as a carrier, and as a result, the present inventors have found the invention which is described herein.

According to the present invention, one or more polypeptides, one or more proteins and one or more physiologically active substances are ground and mixed mechanically in a frozen state, and the blend is shaped into a desired form, and compressed at a pressure of from 100 to 20,000 kg/cm² to thereby produce a slow release composite having the physiologically active substances encapsulated therein. This is the most basic concept of the present invention, and the following are developments and improvements of this concept.

Therefore, according to one feature of the present invention a system comprising a polypeptide, a protein and a physiologically active substance is irradiated with light or ionizing radiation at a temperature between $-70°$ C. and $-100°$ C. under pressure or after compressing it, so as to provide a slow release composite having slower releasability and having the physiologically active substance encapsulated in the matrix made of polypeptide and protein.

One feature of the present invention is to use both polypeptide and protein as the components of a matrix for encapsulating a physiologically active substance. According to the present invention, the polypeptide and protein are heated under pressure to form an apparent film. Therefore, by treating mixed particles of the polypeptide, protein and physiologically active substance under pressure, the physiologically active substance is uniformly dispersed and encapsulated in the film of polypeptide and protein matrix.

DETAILED DESCRIPTION OF THE INVENTION

Figure 1:
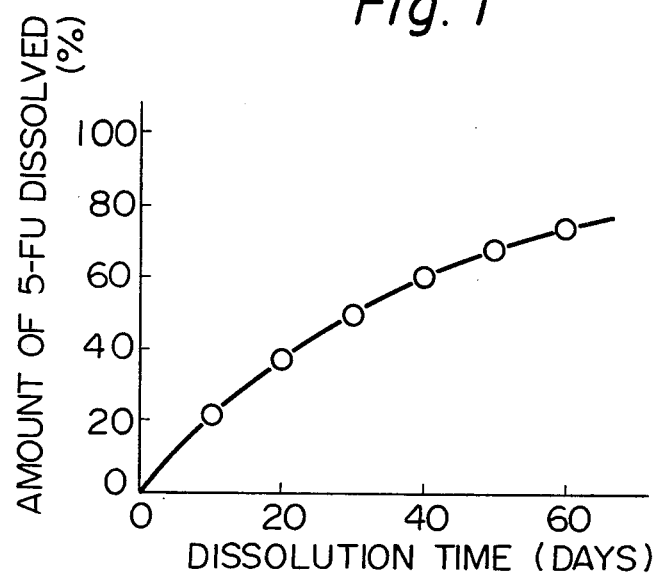
FIGS. 1 to 8 are graphs showing the profile of release of physiologically active substances from the slow release composite samples prepared in Examples 1 to 16 according to the present invention.

The present invention relates to a process for producing a slow release composite. More particularly, the invention relates to a process for producing a slow release composite having a physiologically active substance encapsulated therein by shaping under pressure a system comprising a polypeptide, a protein and the physiologically active substance. The invention also relates to a process for producing a slow release composite having a physiologically active substance encapsulated therein by shaping under pressure and low temperatures a system comprising N-carboxyamino acid anhydride and the physiologically active substance. The invention further relates to a process for producing a slow release composite having a physiologically active substance encapsulated therein by heat-treating a system comprising a polypeptide, a protein, the physiologically active substance and a mixture of water and organic solvent.

In the practice of the present invention, the polypeptide, protein and physiologically active substance can be mixed thoroughly if they are divided into fine particles before the mixing. One technique for obtaining finely divided particles is to grind them in a frozen state at a temperature between $0°$ and $-200°$ C.

In the practice of the present invention, the system comprising the polypeptide, protein and physiologically active substance is irradiated with light or ionizing radiation under pressure after compression. The pressure to be applied is desirably between 50 and 20,000 kg/cm². There is no particular limitation on the type of light and ionizing radiation that can be used in the present invention, but radiation sources having great penetration energy such as gamma-rays from cobalt 60 and beta-rays from strontium 89 are preferred. The adsorbed dose is generally from $5 \times 10^4$ to $5 \times 10^6$ rads, and a dose of about $1 \times 10^6$ serves the purpose. The irradiation temperature is generally $0°$ C. or less, preferably between $-70°$ C. and $-100°$ C. One advantage of using such low irradiation temperatures is that is physiologically active substance is not inactivated and is uniformly distributed within the slow release composite produced.

The present inventors further continued their studies to improve the above described method and reviewed a process for producing a slow release composite by using as a matrix base an N-carboxyamino acid anhydride (hereunder sometimes referred to as NCA) monomer. It is well known that the crystal of NCA polymerizes in atmosphere, as reported in H. Mark, J. Appl. Phys. 20, 531 (1949) and N. H. Grant, J. Am. Chem. Soc., 85, 4071 (1966). In these papers, NCA is polymerized in a solid phase and ionizing radiation is used as a polymerization inducer, but in either paper, only a polymer whose molecular weight is as low as that of oligopeptide is reported. But the studies of the present inventors have revealed that NCA can be converted into a polypeptide by shaping it into a suitable form at a temperature between $-20°$ C. and $40°$ C. and a pressure between 10 and 20,000 kg/cm$^2$, and that the polypeptide can be converted into a product of higher molecular weight by irradiating it with light or ionizing radiation at a temperature between $-100°$ C. and $40°$ C. As one example, the present inventors shaped L-valine NCA monomer into a suitable form at room temperature at 2,000 kg/cm$^2$ and irradiated the shaped product with gamma-rays from Co-60 at $-50°$ C. to give an absorbed dose of 1 Mrad. The molecular weight of the polypeptide was measured in trichloroacetic acid at a concentration of 0.25 g Hl, and it was found to have a high molecular weight (specific viscosity/conc.$=2.2$).

According to the present invention, polypeptide is used as a matrix to encapsulate the physiologically active substance, and the reason for using the polypeptide as a matrix is that it is highly compatible with the living tissue and is easily digested by enzymes. The polypeptide used as the matrix of the slow release composite of the present invention is produced by NCA, but there is no particular limitation on the method of producing NCA. In the practice of the present invention, a polymerizable composition containing NCA is polymerized suitably at a temperature between $-20°$ C. and $40°$ C. This temperature naturally depends on the polymerization time.

The present inventors have made further studies to improve the above described method and found that a slow release composite having even slower releasability, greater hardness and strength can be produced by adding a water-organic solvent system to a mixture of a polypeptide, a protein and a physiologically active substance, shaping the blend into a suitable form, and heating the shaped product at a temperature between room temperature and 100° C.

In the practice of this improved invention, the preferred proportion of the respective components is 10 parts by weight of polypeptide containing 5 to 95 wt% of protein, 0.1 to 10 parts by weight of water containing 0.1 to 95 wt% of an organic solvent and 1 to 100 parts by weight of physiologically active substance. The sequence and method of adding and blending the respective components are not limited to a particular mode. The heating temperature is generally in the range of from room temperature to 100° C., preferably from 30° to 90° C. The temperature naturally depends on the heating time. Therefore, a desired degree of protein denaturation can be obtained by selecting a proper combination of the heating temperature and time. In this improved invention, the slow release composite can be shaped into a film, sheet, granules, powder, rod or other various forms. The physiologically active substance can be formed in several layers having varying concentrations. In one embodiment of the invention, the composite obtained can be irradiated with light or ionizing radiation, and the irradiated composite can release the physiologically active substance over a longer period than the untreated composite, and furthermore, it has a greater hardness and strength. For the radiation source and absorbed dose that can be used in this embodiment, reference can be had to the description in connection with the basic invention and the first improvement on it.

Examples of the physiologically active substance that can be used in the present invention include bleomycin hydrochloride, mitomycin C, adriamycin, carbazyl quinone, rhomstin, diphosphamide, thioiosine, citarabin, fluorouracil, 1-(2-tetrahydrofuryl)-5-fluorouracil, citoteine, chlorambutyl, bibromomannitol, thio-TEPA, cyclophosphamide, acetylurin, noradrenaline, serotonin, callicrein, gastrin, secretin, adrenaline, insulin, glucagon, $\beta$-methazone, indometasine, ACTH, growth hormone, gonadotrophin, oxytocin, vasopressin, thyroxine, testicular hormone, vesicular hormone, luteal hormone, adrenal cortical hormone, prostaglandin, antihistamic, hypotensive agent, vasoconstrictor, capillarly stabilizer, stomachic/digestive, intestinal control agent, contraceptive, dermatologic bacteriocide/disinfectant, agent for treating parasitic dermal diseases, antiinflammatory, vitamins, enzyme preparations, vaccines, antiprotozoan agent, interferon inducing substances, anthelmintic, agent for treating fish diseases, agrichemicals, auxin gibberellin, cidocainine, abietic acid, insect hormone, etc.

Examples of the polypeptide that can be used in the present invention include poly-alanine, poly-glycine, poly-valine, poly-leucine, poly-isoleucine, poly-serine, poly-o-benzyl-serine, poly-threonine, poly-o-benzyl-threonine, poly-cysteine, poly-s-benzyl-cysteine, poly-cystine, poly-methionine, poly-proline, poly-oxyproline, poly-aspartic acid, poly-$\beta$-benzyl-aspartic acid, poly-glutamic acid, poly-$\gamma$-benzyl-glutamic acid, poly-$\Delta$-methyl-glutamic acid, poly-histidine, poly-lysine, poly-oxylysine, poly-ornithine, poly-arginine, poly-nitroalginine, poly-phenylalanine, poly-tyrosine, poly-o-benzyl-tyrosine, and polytryptophan.

The protein used in this invention is derived from various sources such as starch, beta-globulin, gamma-globulin, albumen albumin, milk albumin, bovine serum albumin, human serum albumin, other serum albumins, leucosin, hemoglobin, globin, alpha-lipoprotein, beta-lipoprotein, fibrinogen, ovoalbumin, conalbumin, euglobulin, pseudoglobulin, glutenin, gliadin, insulin, glutathione, pectin, albumen, prolamine, glutelin, histone, protamine, metaprotein, peptone, myoglobin, ferritin, bacteriorhodopsin, rubredoxin, chymotrypsin, ribonuclease, papain, thermolysin, thioredoxin, flavodoxin, hexokinase, phosphorylase, carboxypeptidase A, albumen lysozyme, cytochrome, thrombin, elastase, pepsin, elastin, and protamine.

Examples of the NCA that can be used in the present invention include glycine NCA, alanine NCA, valine NCA, leucine NCA, cysteine NCA, tyrosine NCA, proline NCA, methionine NCA, histidine NCA, thyroxine NCA, aspartic acid NCA, glutamic acid NCA, oxyglutamic acid NCA, lysine NCA, ornithine NCA and arginine NCA. Other amino acids may also be employed if NCA can be produced from them.

Suitable organic solvents that can be used in the present invention are alcohols, organic acids, and any other organic solvent that dissolves or swells the polypeptides and proteins listed above.

The present invention is now described in greater detail by reference to the following examples and comparative examples which are given here for illustrative purposes only and are by no means intended to limit the scope of the invention. In the examples, thests were conducted to see how various physiologically active substances in the slow release composite dissolved into 100 ml of water. The tests were conducted in accordance with USP XIX at 37° C. with a basket rotating at 100 rpm.

EXAMPLE 1

One gram of poly-L-leucine, 0.3 g of milk casein and 700 mg of 5-fluorouracil (5-FU) were divided into fine particles as they were frozen in liquid nitrogen (−196° C.), and were thoroughly mixed by mechanical means. Thereafter, the fine particles were shaped into flat-bottom disc pellets at a pressure of 1200 kg/cm$^2$. A test was conducted to see how 5-FU was released from the pellets in vitro. The release profile is shown in FIG. 1.

EXAMPLES 2 AND 3

Figure 2:
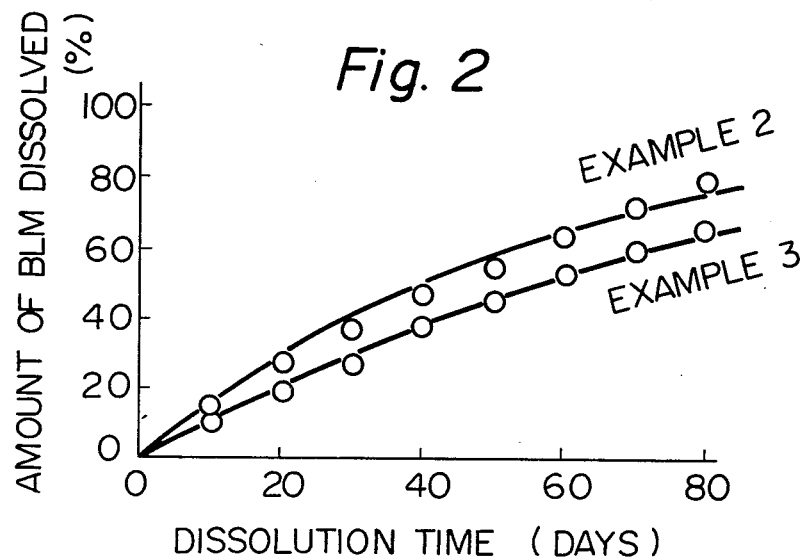

An intimate mixture of 0.7 g of poly-L-glutamic acid, 0.3 g of poly-L-aspartic acid, 0.01 ml of water and 200 mg of bleomycin hydrochloride (BLM) (Example 2) and an intimate mixture of 0.7 g of poly-L-glutamic acid, 0.3 g of poly-L-aspartic acid, 0.01 ml of methanol and 200 mg of bleomycin hydrochloride (BLM) (Example 3) were shaped into flat-bottom disc pellets at a pressure of 2,000 kg/cm$^2$. A test was conducted to see how BLM was replaced from the pellets in vitro. The release profile is shown in FIG. 2.

EXAMPLE 4

Figure 3:
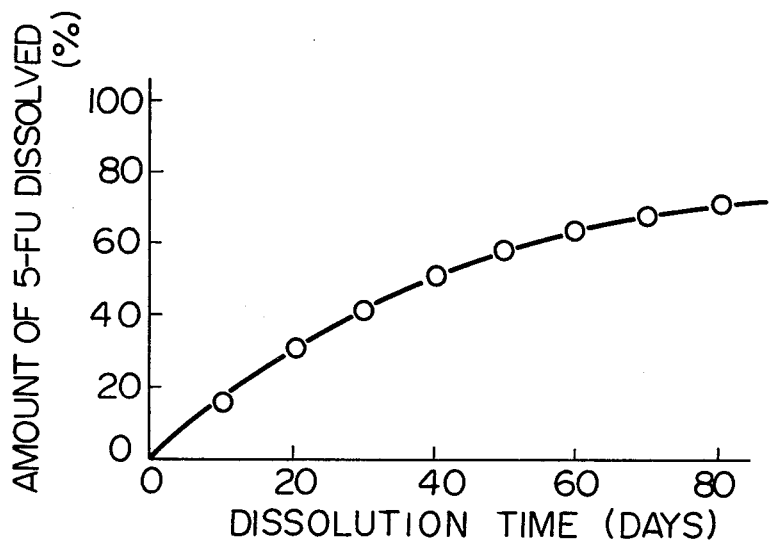

A slow release composite was prepared as in Example 1 except that 1 g of copoly-(glycine-proline) (4:6) was used as polypeptide, and the composite was irradiated with gamma-rays from Co-60 under pressure to give an absorbed dose of 0.5 Mrad. A test was conducted to see how 5-FU was released from composite in vitro. The release profile is shown in FIG. 3.

EXAMPLE 5

Figure 4:
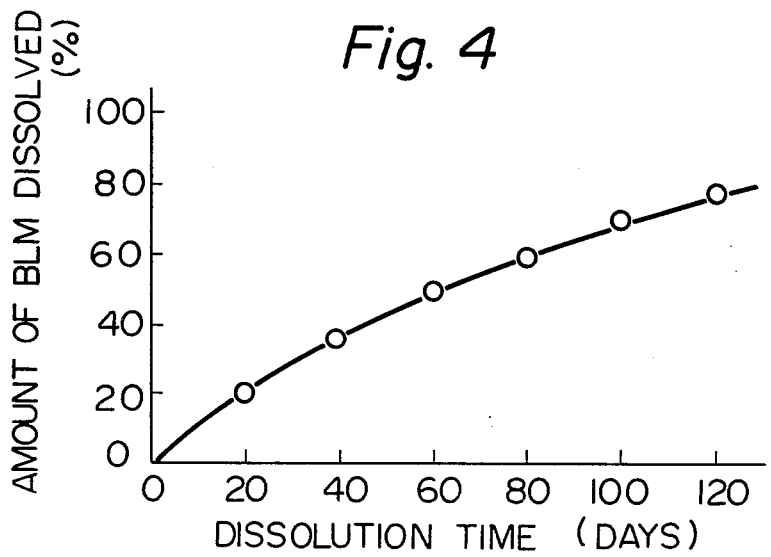

Flat-bottom disc pellets were prepared as in Example 3 except that the compressed pellets were irradiated with gamma-rays from Co-60 at lower than 0° C. to given an absorbed dose of 1 Mrad. A test was conducted to see how BLM was released from the pellets in vitro. The release profile is shown in FIG. 4.

EXAMPLES 6 TO 9

Flat-bottom disc pellets 10 mm in diameter were prepared by heating mixtures of 100 mg of a mixture of poly-ξ-carbobenzoxy-L-lysine and human serum albumin, 50 mg of belomycin hydrochloride (BLM) and a mixture of water and ethyl alcohol at 80° C. for 3 minutes. The formulation of the mixture of poly-ξ-carbobenzoxy-L-lysine and human serum and the mixture of water and ethyl alcohol is indicated below.

| Ex. No. | polypeptide-protein mixture | | water-organic solvent mixture | |
|---|---|---|---|---|
| | poly-ξ-carbobenzoxy-L-lysine (mg) | albumin (mg) | water (ml) | ethyl alcohol (ml) |
| 6 | 30 | 70 | 0.035 | 0.015 |
| 7 | 50 | 50 | 0.020 | 0.010 |
| 8 | 70 | 30 | 0.015 | 0.005 |
| 9 | 50 | 50 | 0.020 | 0.010 |

Figure 5:
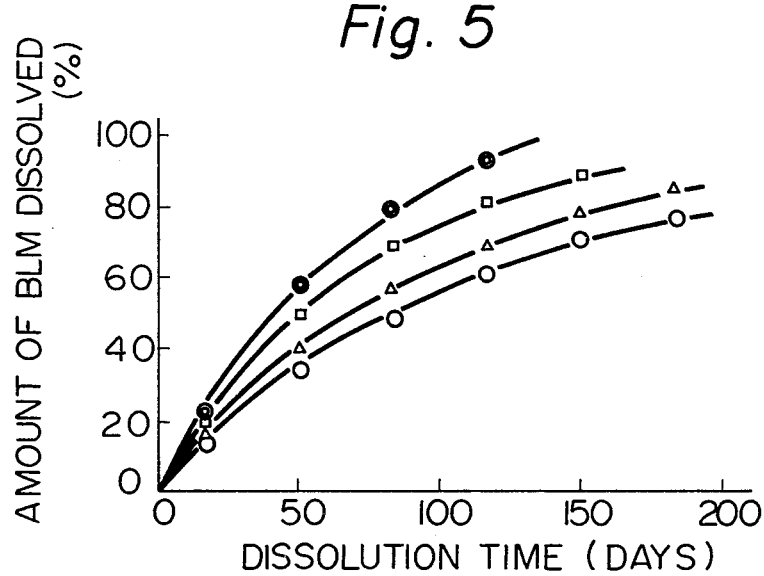

A test was conducted to see how BLM was released from the pellets in vitro. The release profile is shown in FIG. 5.

The pellets prepared in Example 7 were planted under the skin of the back of a group of mice. Four months later, the pellets were recovered, and their weight was 40% of the initial weight. In FIG. 5, the symbols □, o, Δ, and indicate the release profile of the samples prepared in Examples 6, 7, 8 and 9, respectively.

EXAMPLE 10

Figure 6:
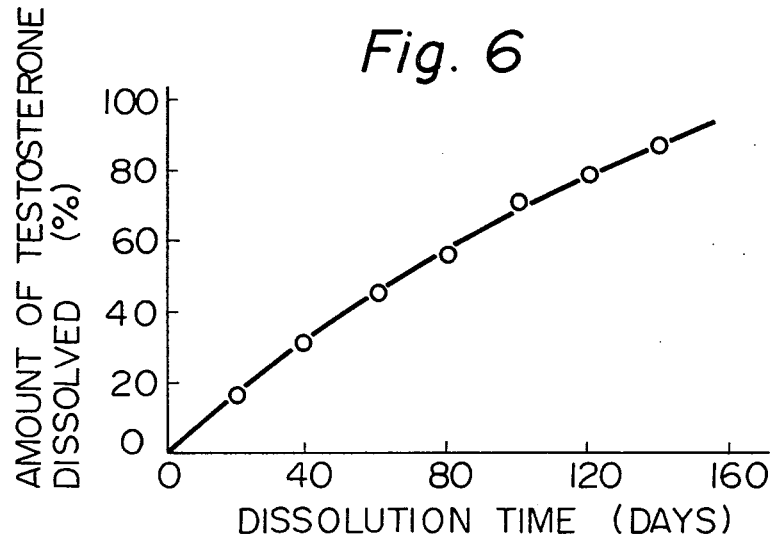

Flat-bottom disc pellets were prepared as in Example 8 using a copolymer of γ-benzyl-L-glutamate and L-leucine as polypeptide, γ-globlin as protein, and testosterone as a physiologically active substance. A test was conducted to see how testosterone was released from the pellets in vitro. The release profile is shown in FIG. 6.

EXAMPLE 11

Flat-bottom disc pellets were prepared in Example 9 except that they were irradiated with gamma-rays from Co-60 at lower than 0° C. to give an absorbed dose of 1 Mrad. A test was conducted to see how BLM was released from the pellets in vitro. The release profile was similar to that obtained for the slow release composite prepared in Example 8.

EXAMPLES 12 AND 13

Figure 7:
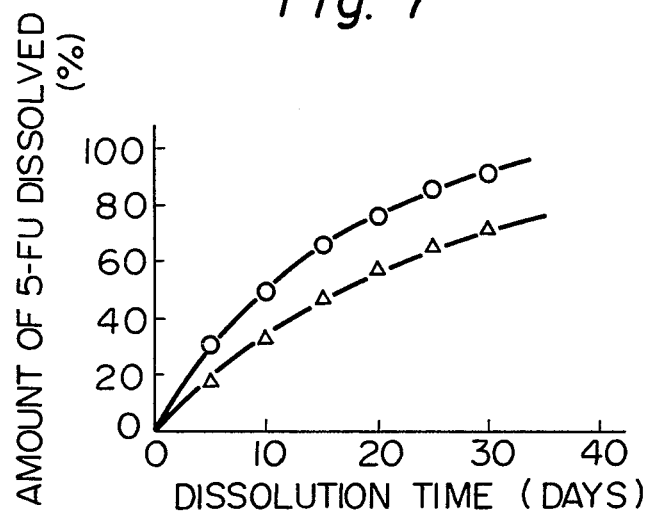

Two intimate particulate mixtures of 300 mg of γ-benzyl-L-glutamate NCA and 300 mg of 5-fluorouracil (5-FU) were shaped at 1,000 kg/cm$^2$ (Example 12) and at 5,000 kg/cm$^2$ (Example 13) at 40° C. and r.h. 60% to produce slow release composites of poly-γ-benzyl-L-glutamate having 5-FU encapsulated therein. A test was conducted to see how 5-FU was released from the composites. The release profile is shown in FIG. 7 wherein the symbols -o- and -Δ- indicate the data for the samples prepared in Examples 12 and 13, respectively.

EXAMPLE 14

Figure 8:
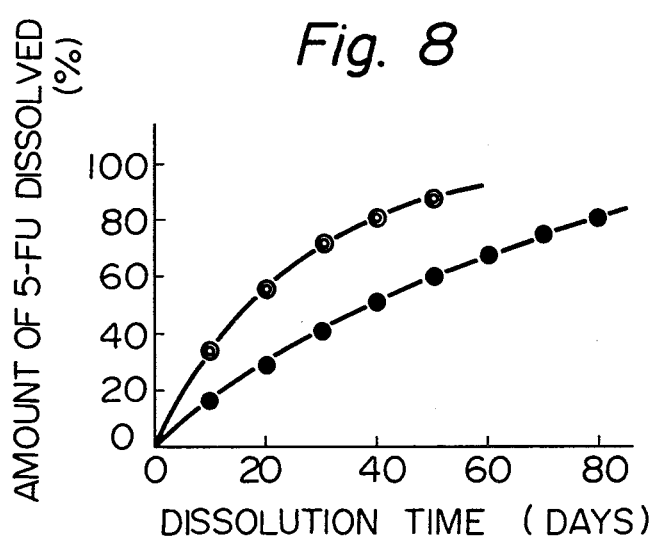

A slow release composite was prepared as in Example 12 except that the γ-benzyl-L-glutamate NCA was replaced by a mixture of 150 ml of L-leucine NCA and 150 mg of L-valine NCA. A test was conducted to see how 5-FU was released from the composite. The release profile is shown in FIG. 8 by the symbol .

EXAMPLE 15

A slow release digestive composite of copoly-(L-leucine, L-valine) having 5-FU encapsulated therein was prepared as in Example 14 except that it was irradiated with gamma-rays from Co-60 at −30° C. to given an absorbed dose of 1 Mrad. A test was conducted to see how 5-FU was released from the composite. The release profile is shown in FIG. 8 by the symbol . The composite was planted under the dorsal skin of mice. Four months later, the weight of the sample recovered from the mice was 60% of the initial value.

EXAMPLE 16

A slow release composite was prepared as in Example 15 except that 5-FU was replaced by mitomycin C (MMC). A test was conducted to see how MMC was released from the composite. The release profile was similar to that obtained for the sample prepared in Example 15.

What is claimed is:
1. A process for producing a slow release composite having a physiologicaly active substance encapsulated therein, wherein a system comprising one or more polypeptides selected from the group consisting of poly-alanine, poly-glycine, poly-valine, poly-leucine, polyisoleucine, poly-serine, poly-o-benzyl-serine, poly-threonine, poly-o-benzyl-threonine, poly-cysteine, poly-s-benzyl-cysteine, poly-cystine, poly-methionine, poly-proline, poly-oxyproline, poly-aspartic acid, poly-β-benzyl-aspartic acid, poly-glutamic acid, poly-γ-benzyl-glutamic acid, poly-γ-methyl-glutamic acid, poly-histidine, poly-lysine, poly-oxylysine, poly-ornithine, poly-arginine, poly-nitroalginine, poly-phenylalanine, poly-tyrosine, poly-o-benzyl-tyrosine, and polytryptophan, one or more proteins selected from the group consisting of starch, beta-globulin, gamma-globulin, albumen albumin, milk albumin, bovine serum albumin, human serum albumin, other serum albumins, leucosin, hemoglobin, globin, alpha-lipoprotein, beta-lipoprotein, fibrinogen, ovalbumin, conalbumin euglobulin, pseudoglobulin, glutenin, gliadin, insulin, glutathione, pectin, albumen, prolamine, glutelin, histone, protamine, metaprotein, peptone, myoglobin, ferritin, bacteriorhodopsin, rubredoxin, chymotrypsin, ribonuclease, papain, thermolysin, thioredoxin, flavodoxin, hexokinase, phosphorylase, carboxypeptidase A, albumen lysozyme, cytochrome, thrombin, elastase, pepsin, elastin, and protamine, and one or more physiologically active substances is ground into particles and mixed mechanicaly in a frozen state, the blend is shaped into a suitable form, and the shaped article is compressed into a suitable form at a pressure of from 100 to 20,000 kg/cm².

2. A process for producing a slow release composite having physiologically active substance encapsulated therein, wherein a system comprising one or more polypeptides selected from the group consisting of poly-alanine, poly-glycine, poly-valine, poly-leucine, polyisoleucine, poly-serine, poly-o-benzyl-serine, poly-threonine, poly-o-benzyl-threonine, poly-cysteine, poly-s-benzyl-cysteine, poly-cystine, poly-methionine, poly-proline, poly-oxyproline, poly-aspartic acid, poly-β-benzyl-aspartic acid, poly-glutamic acid, poly-γ-benzyl-glutamic acid, poly-γ-methyl-glutamic acid, poly-histidine, poly-lysine, poly-oxylysine, poly-ornithine, poly-arginine, poly-nitroalginine, poly-phenylalanine, poly-tyrosine, poly-o-benzyl-tyrosine, and polytryptophan, one or more proteins selected from the group consisting of starch, beta-globulin, gamma-globulin, albumen albumin, milk albumin, bovine serum albumin, human serum albumin, other serum albumins, leucosin, hemoglobin, globin, alpha-lipoprotein, beta-lipoprotein, fibrinogen, ovalbumin, conalbumin euglobulin, pseudoglobulin, glutenin, gliadin, insulin, glutathione, pectin, albumen, prolamine, glutelin, histone, protamine, metaprotein, peptone, myoglobin, ferritin, bacteriorhodopsin, rubredoxin, chymotrypsin, ribonuclease, papain, thermolysin, thioredoxin, flavodoxin, hexokinase, phosphorylase, carboxypeptidase A, albumen lysozyme, cytochrome, thrombin, elastase, pepsin, elastin, and protamine, and one or more physiologically active substances is ground into particles and mixed mechanicaly in a frozen state, the blend is shaped into a suitable the shaped article is compressed into a suitable form at a pressure of from 100 to 20,000 kg/cm², said shaped article being irradiated with light or ionizing radiation as it is compressed or after it has been compressed at a pressure of from 100 to 20,000 kg/cm².

3. A process for producing a slow release composite having physiologically active substance encpsulated therein, wherein a system comprising one or more polypeptides selected from the group consisting of poly-aniline, poly-glycine, poly-valine, poly-leucine, polyisoleucine, poly-serine, poly-o-benzyl-serine, poly-threonine, poly-o-benzyl-threonine, poly-cysteine, poly-s-benzyl-cysteine, poly-cystine, poly-methionine, poly-proline, poly-oxyproline, poly-aspartic acid, poly-β-benzyl-aspartic acid, poly-glutamic acid, poly-γ-benzyl-glutamic acid, poly-γ-methyl-glutamic acid, poly-histidine, poly-lysine, poly-oxylysine, poly-ornithine, poly-arginine, poly-nitroalginine, poly-phenylalanine, poly-tyrosine, poly-o-benzyl-tyrosine, and polytryptophan, one or more proteins selected from the group consisting of starch, beta-globulin, gamma-globulin, albumen albumin, milk albumin, bovine serum albumin, human serum albumin, other serum albumins, leucosin, hemoglobin, globin, alpha-lipoprotein, beta-lipoprotein, fibrinogen, ovalbumin, conalbumin euglobulin, pseudoglobulin, glutenin, gliadin, insulin, glutathione, pectin, albumen, prolamine, glutelin, histone, protamine, metaprotein, peptone, myoglobin, ferritin, bacteriorhodopsin, rubredoxin, chymotrypsin, ribonuclease, papain, thermolysin, thioredoxin, flavodoxin, hexokinase, phosphorylase, carboxypeptidase A, albumen lysozyme, cytochrome, thrombin, elastase, pepsin, elastin, and protamine.

one or more physiologically active substances, and a suitable mixture of water and an organic solvent is shaped into a suitable form, and the shaped article is heated at a temperature between room temperature and 100° C.

4. A process for producing a slow release composite having a physiologically active substance encapsulated therein, wherein a system comprising one or more polypeptides selected from the group consisting of poly-alanine, poly-glycine, poly-valine, poly-leucine, polyisoleucine, poly-serine, poly-o-benzyl-serine, poly-threonine, poly-o-benzyl-threonine, poly-cysteine, poly-s-benzyl-cysteine, poly-cystine, poly-methionine, poly-proline, poly-oxyproline, poly-aspartic acid, poly-β-benzyl-aspartic acid, poly-glutamic acid, poly-γ-benzyl-glutamic acid, poly-γ-methyl-glutamic acid, poly-histidine, poly-lysine, poly-oxylysine, poly-ornithine, poly-arginine, poly-nitroalginine, poly-phenylalanine, poly-tyrosine, poly-o-benzyl-tyrosine, and polytryptophan, one or more proteins selected from the group consisting of starch, beta-globulin, gamma-globulin, albumen albumin, milk albumin, bovine serum albumin, human serum albumin, other serum albumins, leucosin, hemoglobin, globin, alpha-lipoprotein, beta-lipoprotein, fibrinogen, ovalbumin, conalbumin euglobulin, pseudoglobulin, glutenin, gliadin, insulin, glutathione, pectin, albumen, prolamine, glutelin, histone, protamine, metaprotein, peptone, myoglobin, ferritin, bacteriorhodopsin, rubredoxin, chymotrypsin, ribonuclease, papain, thermolysin, thioredoxin, flavodoxin, hexokinase, phosphorylase, carboxypeptidase A, albumen lysozyme, cytochrome, thrombin, elastase, pepsin, elastin, and protamine,
one or more physiologically active substances, and
a suitable mixture of water and an organic solvent is shaped into a suitable form, and the shaped article is heated at a temperature between room temperature and 100° C., and the heated product is further irradiated with light or ionizing radiation.

* * * * *